United States Patent [19]

Häberlein

[11] 4,314,203
[45] Feb. 2, 1982

[54] TEST ARRANGEMENT FOR THE NON-DESTRUCTIVE TESTING OF METALLIC TEST PIECES

[75] Inventor: Peter Häberlein, Reutlingen, Fed. Rep. of Germany

[73] Assignee: Institut Dr. Friedrich Förster Prüfgerätebau, Fed. Rep. of Germany

[21] Appl. No.: 27,711

[22] Filed: Apr. 9, 1979

[30] Foreign Application Priority Data

Apr. 8, 1978 [DE] Fed. Rep. of Germany ....... 2815228

[51] Int. Cl.³ .................. G01R 33/00; G01N 27/82
[52] U.S. Cl. ................................. 324/262; 324/238
[58] Field of Search ............ 324/228, 234, 237, 238, 324/240, 241, 242, 243, 262, 217, 218

[56] References Cited

U.S. PATENT DOCUMENTS

| | | | |
|---|---|---|---|
| 2,219,885 | 10/1940 | Barnes et al. | 324/260 |
| 3,244,972 | 4/1966 | Fisher | 324/226 |
| 3,311,819 | 3/1967 | Miller. | |
| 3,593,120 | 7/1971 | Mandula et al. | |
| 4,041,379 | 8/1977 | Karlsson | 324/242 |

FOREIGN PATENT DOCUMENTS

| | | | |
|---|---|---|---|
| 2050827 | 4/1972 | Fed. Rep. of Germany. | |
| 2556269 | of 0000 | Fed. Rep. of Germany. | |
| 508730 | 3/1976 | U.S.S.R. | 324/262 |

Primary Examiner—Gerard R. Strecker
Assistant Examiner—Walter E. Snow
Attorney, Agent, or Firm—George J. Netter

[57] ABSTRACT

A test arrangement for non-destructive defect testing of metallic test pieces includes test probes which contactingly move across the surface of a test piece. Resilient members act on the testhead carrying the probes, one at each side of the testhead center of gravity, enabling the testhead to extend beyond the test piece edge while maintaining good contact between the probes and test piece. The testhead is adjustable with respect to the test piece surface and is maintained at a constant spacing from the test piece irrespective of test piece surface irregularities.

12 Claims, 3 Drawing Figures

TEST ARRANGEMENT FOR THE NON-DESTRUCTIVE TESTING OF METALLIC TEST PIECES

The present invention relates to a test arrangement for the non-destructive testing of test pieces, in particular slabs, billets and the like, for surface irregularities, in which traction means move along the test piece surface and carry testhead mounting means with a testhead having one or several test probes. The testhead whose bottom is suited for sliding contact with the test piece surface and which is towed by the testhead mounting means, the horizontal forces encountered between the testhead mounting means and the testhead being absorbed by a hinge joint which permits the testhead to swing at least about one axis extending vertically in relation to the direction of movement and parallel to the test piece surface, and the vertical forces encountered between the testhead mounting means and the testhead being absorbed by separate connection means.

In one known arrangement, which conforms largely to the species described above and which has been described in German Laid-Open Patent Application No. 24 39 662, a variable contact pressure is applied upon the testhead by a first connecting link of variable length which is arranged in vertical relation to the test piece surface, while a second connecting link extending in parallel relation to the test piece surface is pivotally connected to the testhead, thus preventing the latter from moving in vertical relation to the travelling direction and in parallel relation to the test piece surface.

Arrangements of this type are employed for determining and, in certain cases, for colour-marking any defects encountered near the test piece surface so that such defects may be corrected before the subsequent processing steps.

The defect signal converters used in such arrangements are the most different types of probes employed in the field of non-destructive materials testing, being preferably however magnetic or inductive magnetic probes. The latter are arranged within the testhead directly above its bottom and considering that the testhead performs a sliding movement along the test piece surface, they are in a position to maintain an essentially constant distance from the test piece surface, and this is necessary to insure an essentially uniform sensitivity of the probes. Due to unevenness and curvature in the test piece surface, which are always encountered in practice, it is necessary that the testhead has at least one axis of freedom, that is the testhead must be permitted to swing at least about one axis in vertical relation to the direction of movement and in parallel relation to the test piece surface, to enable the testhead bottom to follow the surface curvatures.

It is of course desirable that the tested area be extended as closely to the test piece edges as possible. Accordingly, it is often requested that at the moment of application to and lifting off from the test piece, the testhead be allowed to protrude over the edge of the test piece. The necessary amount of protrusion of the testhead may well exceed half the testhead bottom area. It will be particularly great in cases where several probes or probe systems are aligned in the testhead with the direction of movement. This may be the case where different types of defects, such as differently directed defects, are to be detected by different probes. In the known arrangement, the admissible amount of protrusion is determined by the two torques acting around the edge of the test piece as a result of the weight and the vertical contact pressure. when the torque acting beyond the edge of the test piece dominates, the testhead will tilt about the edge of the test piece, causing the test piece bottom and with it the probes to get out of contact with the test piece surface so that the sensitivity of the probes will be reduced or fully eliminated. A displacement in the direction of movement of the point of attack of the vertical contact pressure in relation to the centre of gravity of the testhead will of course increase the admissible amount of protrusion on one side. At the same time, however, it will reduce it on the other side by the same amount. In cases where only gravity forces are to be considered, that is where no vertical contact pressure is applied, the centre of gravity of the testhead may be displaced outwardly as far as to the edge of the test piece.

SUMMARY OF THE INVENTION

It is an object of the present invention to provide an arrangement in which the testhead is allowed to protrude a maximum amount over the test piece edge, without impairing thereby notably the contact between the testhead bottom and the test piece surface.

In such an arrangement, large amounts of protrusion become possible, while at the same time the tilting angles between the protruding testhead bottom and the test piece surface are kept within negligible limits. This results in minimum friction and wear for the testhead bottom. Nevertheless, the solution of the invention can be realized by simple means and without excessive costs.

DESCRIPTION OF THE DRAWINGS

For the better understanding of the invention, certain examples will be described hereafter with reference to the drawing in which.

DESCRIPTION OF A PREFERRED EMBODIMENT

Figure 1:
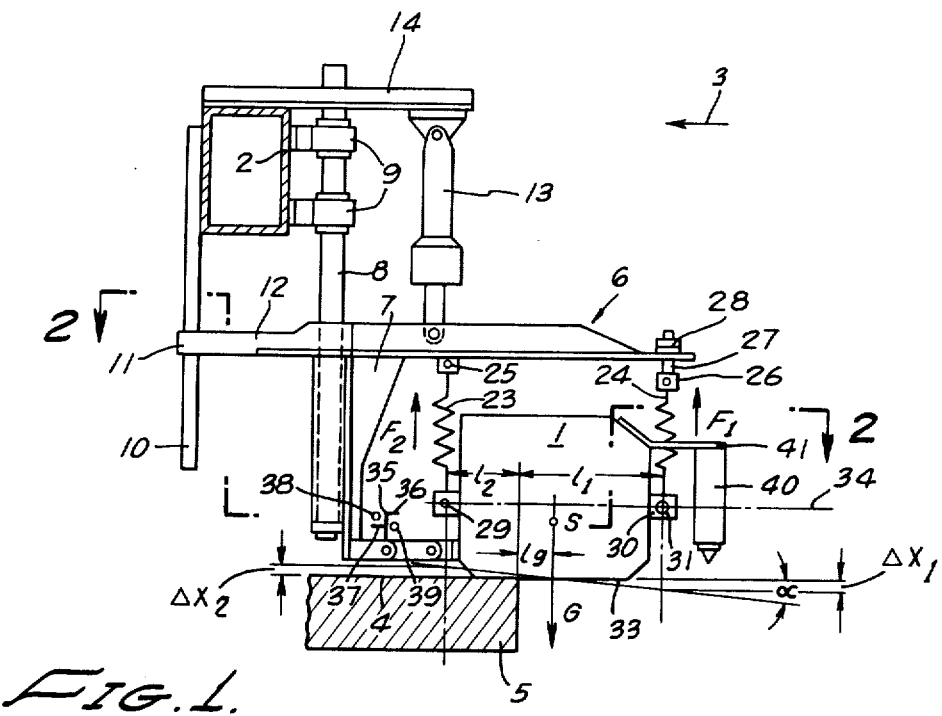
FIG. 1 is a side elevation of a test arrangement
Figure 2:
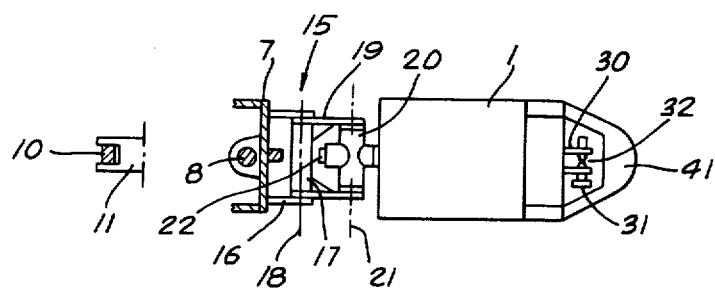
FIG. 2 is a top view of the testhead of the test arrangement of FIG. 1

FIGS. 1 and 2 show a simplified representation of an arrangement for testing slabs.

A number of testheads (1), which are provided in staggered arrangement in relation to the plane of the drawing, are towed in the direction indicated by arrow (3) over the surface (4) of the slab (5) by common traction means of which, for simplicity's sake only the traverse (2) is shown. Within each testhead (1), two inductive magnetic test probes are mounted closely above the testhead bottom (33). The exact positioning of the probes will be explained below. Each testhead (1) is associated with testhead mounting means (6) comprising essentially an angular frame (7) and a shaft (8). The latter is seated in a thrust bearing (9) mounted at the traverse (2). Likewise mounted at the traverse (2) is a square rod (10) which guides the testhead mounting means (6) in the direction of movement, sliding in a fork-shaped support (11) provided at the outer end of an extension (12) of the angular frame (7). The adjustment of the height of the testhead mounting means (6) is ensured by a hydraulic cylinder (13) which has its one end pivotally connected to the horizontal arm of the angular frame (7) and which has its other end pivotally connected to a rail (14) rigidly fastened to the traverse (2).

The hinge connection between the testhead mounting means (6) and the testhead (1) is ensured by a double crosshead (15) which can best be seen in FIG. 2. This double crosshead guides the testhead (1) exactly in the direction of movement (3) while it provides freedom of movement in two planes vertically to each other and to the plane of drawing shown in FIG. 2. Thus, it allows the testhead to adapt itself optimally to any unevenness in the test piece surface (4). The hinge joint comprising the double crosshead (15) is designed as follows: a member (17) is mounted for rotation about an axis (18) between two brackets (16) fastened to the frame (7). A cross-fitting (20) is mounted for rotation about an axis (21) between two arms (19) of the U-shaped element (17). The cross-fitting (20) in turn is rotatably connected to a pin (22) which is rigidly mounted at the testhead (1).

In addition to the above hinge connection, two spiral springs (23, 24) are provided to interconnect the testhead (1) and the testhead mounting means (6). The spiral springs (23, 24) have their upper ends suspended at the frame (7) by means of a rigid plate (25) and an adjustable arrangement comprising a plate (26), a threaded bolt (27) and nuts (28), respectively, whereas the lower ends of the spiral springs (23, 24) are connected to the testhead (1) (1) via a plate (29) and a threaded bolt (31) seated between two plates (30), respectively. This arrangement enables the point of attack of the spiral spring (24) to be laterally adjusted by turning the threaded bolt (31) whose groove (32) holds the spring. When adjusting the system, the bottom (33) of the testhead (1) which is freely suspended on the spiral springs (23, 24) and out of contact with the slab, is brought in parallel relation to the slab surface (4) by turning the threaded bolts (27, 31). It has been found advantageous to have the axis of rotation (34) which forms the connection between the points of attack of the spiral springs (23, 24) only a small distance above the centre of gravity (S) of the testhead (1).

This provides on the one hand a stable centre position of the testhead (1), and on the other hand free motion of the latter about the axis of the bolt (22). A sheet metal piece (41) arranged at the testhead (1) serves as mounting means for a colour-marking device (40) which, controlled by the signals emitted by the test probes, marks in the known manner any defects encountered in the slab surface (5).

In FIG. 1, the centre of gravity (S) protrudes by an amount (1 g) over the edge of the slab (5). The distances $L_1$ and $L_2$ between the plane of the edge and the points of action of the springs (23, 24) may, in the example shown, exhibit a ratio of 2:1. In this case, the tilting angle $\alpha$ between the bottom (33) and the slab surface should not exceed a value of approx. 2°. A simple calculation shows that this is well possible. Although the centre of gravity (S) of the testhead (1) need not necessarily be found in the middle between the points of action of the springs (23, 24) we assume, for simplicity's sake, a symmetrical load distribution.

As regards the spring forces $F_{10}$, $F_{20}$ the following formula applies:

$$F_{10} = F_{20} = \tfrac{1}{2}G = C \cdot x_o \quad (1)$$

wherein (G) is the weight, (C) is the spring stiffness and ($x_o$) is the basic deflection, with the testhead (1) freely suspended. The application of the testhead (1) to the test surface reduces the spring deflection in average by the amount x, thus decreasing the spring forces to $$F_{1x} = F_{2x} = C(x_o - x) \quad (2)$$

The equilibrium of the momenta is determined by the following formula:

$$(F_{1x} + \Delta F_{1x}) \cdot L_1 = (F_{2x} - \Delta F_{2x}) \cdot L_2 + G \cdot lg \quad (3)$$

or $$[C(x_o - x) + C \cdot \Delta x_1] \cdot L_1 = [C(x_o - x) - C \cdot \Delta x_2] \cdot L_2 + G \cdot lg \quad (4)$$

wherein $\Delta F_{1x}$ and/or $\Delta F_{2x}$ are the additional or differential spring force and $\Delta x_1$ and/or $\Delta x_2$ are the additional or differential deflection.

Considering further that $$\tan \alpha = \Delta x_2 / L_2 = \Delta x_1 / L_1 \quad (5)$$

$$\Delta x_2 = (L_2/L_1) \cdot \Delta x_1 \quad (6)$$

and that because of the symmetry of loads:

$$2lg = L_1 - L_2 \quad (7)$$

and that because of (1)

$$x_o = G/2C \quad (8)$$

the following formula is obtained:

$$\tan \alpha = \frac{\Delta x_1}{L_1} = x \cdot \frac{L_1 - L_2}{L_1^2 + L_2^2} \quad (9)$$

The value x in this formula is conveniently selected greater than the maximum spring deflections to be expected as a result of unevenness of the slab surface (4). In the present example, it has been supposed that x = 10 mm, $L_1$ = 200 mm and $L_2$ 0 100 mm. Thus, an angle $\alpha = 1°10'$ is obtained.

A further factor of influence for sizing considerations is the residual contact pressure which should exceed the frictional forces encountered in particular within the joints.

The residual contact pressure is equal to the difference between the weight (G) of the testhead (1) and the sum of the spring forces $F_1 + F_2$, with the testhead (1) in surface contact and considering the permissible maximum deflection of the springs (23, 24) caused by unevenness of the test piece surface (4).

It is of utmost importance that the point of action of the two springs be maintained constant at the selected value $x_o - x$ during the travel of the testhead (1) over the slab (5). This means that mere level variations within the surface of a slab or differences in the thickness of different slabs should not cause any reduction or extension of the spring length (23, 24). In the example shown in FIGS. 1 and 2, simple regulating means are provided for keeping the point of action of the springs constant. The transmitter of this system takes the form of a lever (35) fixed at the member (17) of the crosshead (15). This lever is provided with two signal lugs (36, 37) coacting with proximity sensors (38, 39), which in turn are connected by transmission members to the hydraulic cylinder (13) which can be actuated in two directions. As soon as the lever (35) deviates from its medium position as shown in the drawing, one of the two signal lugs (36, 37) will mask its associated proximity sensor (38 or 39), thus releasing a signal in the masked proximity sensor. The medium position of the lever (35) corresponds to the intended point of action of the springs (23, 24). When the testhead (1) rises or lowers itself in response to a change in the level of the test piece surface, this movement is transmitted to the lever (35) through the member (17). The signal of one of the two proximity sensors (38, 39) released by the lever (35) causes the hydraulic cylinder (13) to raise or lower the testhead mounting means (6) until the lever occupies again its centre position. In this manner, the previous point of action of the springs (23, 24) can be restored and continuously maintained.

Figure 3:
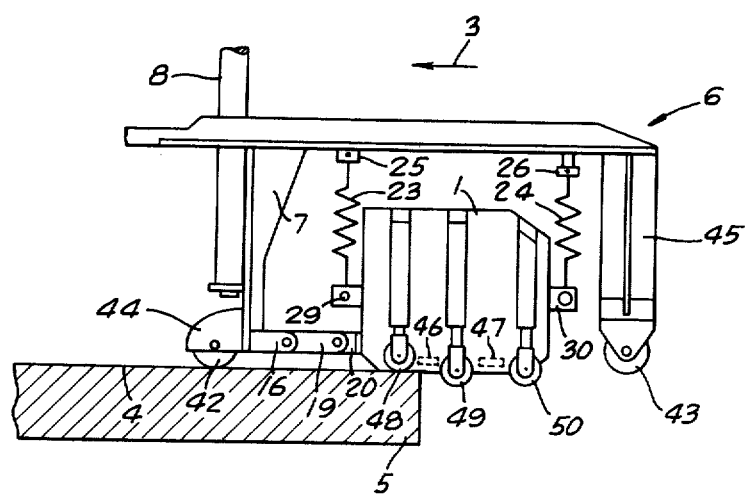
FIG. 3 shows an alternative embodiment.

In many cases, an even simpler device, as shown for instance in FIG. 3, may be used for keeping the height of the testhead mounting means above the test piece surface constant. The testhead (1) and its connection to the testhead mounting means (6) may be principally the same as described above. However, the control system is replaced by supporting means comprising two supporting wheels (42, 43) the first of which has its wheel case (44) fastened to the vertical arm of the angular frame (7) of the testhead mounting means (6), whereas the second is mounted to the horizontal leg of the angular frame (7) via an arm (45). The testhead mounting means (6), which is guided by the shaft (8) of the towing means in essentially parallel relation to the test piece surface (4) is thus in any case supported against the test piece surface (4) by one of the two supporting wheels (42, 43), that is by the supporting wheel (42) when the testhead (1) protrudes rearwardly over the test piece, and by the supporting wheel (43) when the testhead protrudes forwardly over the test piece. Although the distance between the supporting wheels and the testhead centre need not be as large as shown in FIG. 3, the active area of the test probes (46, 47), must not be exceeded by the supporting rollers if the slab (5) is to be tested right to its edge. FIG. 3 shows the position of two test probes (46, 47) arranged in a line in the direction of movement. It is readily apparent that the testhead (1) will have to protrude far beyond the test piece edge if the edge of the slab (5) is to be included in the testing procedure.

Further, FIG. 3 shows three sensors (48, 49, 50) arranged within the testhead (1), one before, another between and a third one behind the probes—always viewed in the direction of movement (3). The sensors (48, 49, 50) emit a particular signal when their sensing wheel is raised as a result of their contact with the test piece. They serve the purpose to switch on the associated test channel when the full area of one of the probes is positioned above the slab surface (4). This is the case for the probe (46) when the test piece sensors (48 and 49) are in their raised position, and for the probe (47) when the sensors (49 and 50) are in their raised position. The above object can be easily achieved by a logical AND circuit for the signals of the test piece sensors (48 and 49 or 49 and 50, respectively).

I claim:

1. In a test arrangement for the non-destructive defect testing of metallic test pieces, in particular slabs, billets and the like having surface irregularities, traction means move along the test piece surface carrying testhead mounting means with a testhead having at least one test probe, the bottom of the test probe being suited for sliding contact with the test piece surface and said testhead being towed by the testhead mounting means, the horizontal forces encountered between the testhead mounting means and the testhead being absorbed by a hinge joint which permits the testhead to swing at least about one axis vertical to the direction of movement and parallel to the test piece surface, and the vertical forces encountered between the testhead mounting means and the testhead being absorbed by separate connection means, the improvement comprising:

the separate connection means including two resilient elements acting upon the testhead, one at each side of the center of gravity of the testhead viewed along the direction of movement, the connecting line between the two points where said resilient elements act upon said testhead being located at a level higher than that of the testhead center of gravity, said testhead being urged toward the test piece by gravity and said two resilient means providing a resilient force opposing gravity;

means for varying the height of the testhead mounting means in relation to the traction means; and means for keeping the testhead mounting means at a constant spacing with respect to the test piece surface.

2. An arrangement as in claim 1, in which the means for keeping the testhead mounting means at a constant level above the test piece surface includes two supporting rollers acting upon the test piece surface in front of and behind a center portion of the testhead as viewed in the movement direction.

3. An arrangement as in claim 1, in which the means for keeping the testhead mounting means at a constant level above the test piece surface includes a control system with sensing means for generating signals indicating the height of the testhead mounting means and with adjusting means for varying the height of the testhead mounting means in response to said signals.

4. An arrangement as in claim 3, in which the adjusting means includes a fluid operated cylinder.

5. An arrangement as in claim 3 in which the sensing means for generating the signals includes a lever mounted at the link joint between the testhead and the testhead mounting means.

6. An arrangement as in claim 1, in which the resilient elements include coil springs.

7. An arrangement as in claim 1, in which the height difference between the line connecting the two points where the resilient elements act upon the testhead and the testhead center of gravity is smaller than the height difference between the center of gravity and the testhead bottom.

8. An arrangement as in claim 1, in which at least one of the points where the resilient elements act upon the testhead can be adjustably displaced across the movement direction and in parallel to the test piece surface.

9. An arrangement as in claim 1, in which the tension of at least one of said resilient elements can be adjusted.

10. An arrangement as in claim 6, in which the residual contact pressure including the difference between the weight of the testhead and the summation of spring forces, with the testhead in contact with the test piece surface, and considering the maximum deflection of the resilient elements caused by irregularities in the test piece surface is greater than the maximum frictional forces encountered.

11. An arrangement as in claim 6, in which the spring tension is adjusted to insure that the bottom of the testhead when freely suspended over the test piece surface extends parallel to the latter.

12. An arrangement as in claim 1, in which two probes are arranged within the testhead aligned with the direction of movement, and three sensors for signaling the contact between the testhead bottom and the test piece surface are likewise arranged aligned with the direction of movement within the testhead such that the first of said probes is located between the foremost and the medium sensors and that the second probe is located between the medium and rearward sensors.

* * * * *